United States Patent [19]

Parker et al.

[11] Patent Number: 5,342,936
[45] Date of Patent: Aug. 30, 1994

[54] TETRA-AZA MACROCYCLES AND PROCESSES FOR THEIR PREPARATION

[76] Inventors: David Parker, 12 East Atherton Street, Durham DH1 4DG; Michael A. W. Eaton, Nethercote, Chinner Road, Aston Rowante, Oxfordshire OX9 5SH, both of United Kingdom

[21] Appl. No.: 964,117

[22] Filed: Oct. 2, 1992

Related U.S. Application Data

[63] Continuation of Ser. No. 826,669, Jan. 29, 1992, abandoned, which is a continuation of Ser. No. 601,705, Oct. 30, 1990, abandoned.

[30] Foreign Application Priority Data

Feb. 10, 1989 [GB] United Kingdom ............ 8903023.3

[51] Int. Cl.$^5$ ............................................ C07D 255/02
[52] U.S. Cl. ...................................... 540/474; 540/465
[58] Field of Search .............................. 540/465, 474

[56] References Cited

U.S. PATENT DOCUMENTS

| | | | |
|---|---|---|---|
| 4,174,319 | 11/1979 | Kobuke | 260/239 |
| 4,174,428 | 11/1979 | Tabushi et al. | 540/474 |
| 4,432,907 | 2/1984 | Wieder et al. | 436/500 |
| 4,472,509 | 9/1984 | Gansow et al. | 436/548 |
| 4,659,839 | 4/1987 | Nicolotti et al. | 548/546 |
| 4,671,958 | 7/1987 | Rodwell et al. | 514/2 |
| 4,678,667 | 7/1987 | Meares | 424/85 |
| 4,702,998 | 10/1987 | Tanaka et al. | 430/430 |
| 4,877,600 | 10/1989 | Bonnemain et al. | 257/2 |
| 4,885,363 | 12/1989 | Tweedle et al. | 540/465 |
| 5,049,667 | 9/1991 | Schaefer et al. | 540/474 |
| 5,053,503 | 10/1991 | Dean et al. | 540/474 |

FOREIGN PATENT DOCUMENTS

| | | | |
|---|---|---|---|
| 76267/87 | 2/1988 | Australia. | |
| 0255471 | of 0000 | European Pat. Off.. | |
| 0173629 | 8/1985 | European Pat. Off.. | |
| 0188256 | 7/1986 | European Pat. Off.. | |
| 0232751 | 8/1987 | European Pat. Off. | 540/474 |
| 88/08422 | 11/1988 | PCT Int'l Appl.. | |
| 89/01476 | 2/1989 | PCT Int'l Appl.. | |
| 1098937 | 6/1984 | U.S.S.R. | 540/474 |

OTHER PUBLICATIONS

Khaw et al., *Science* 209, 295 (1980).
Stetter, H., et al., *Agnew. Chem. Int. Ed. Engl.*, 15, 686 (1976).

(List continued on next page.)

*Primary Examiner*—Mukund J. Shah
*Assistant Examiner*—Y. N. Gupta

[57] ABSTRACT

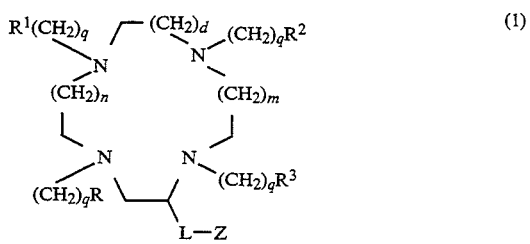

Tetra-aza macrocycles of formula (I), wherein m and n, which may be the same or different, is each zero or an integer 1, 2, or 3; d is zero or an integer 1, 2 or 3; q is zero or an integer from 1 to 6 inclusive; R, $R^1$, $R^2$ and $R^3$, which may be the same or different, is each a hydrogen atom or a group —P(O)(XH)$R^4$ (where X is an oxygen or sulphur atom and $R^4$ is a hydrogen atom or an alkyl or alkoxy group), with the proviso that at least one of R, $R^1$, $R^2$ and $R^3$ is a —P(O)(XH)$R^4$ group; L is a covalent bond or a linker group; Z is a hydrogen atom or a reactive functional group; and metal complexes and/or salts thereof; are described together with processes for their preparation and compositions containing them. The compounds are useful for imaging and in the treatment of abnormal cell disorders, such as in the treatment of tumours, and may be coupled to other molecules, such as proteins for use in diagnosis and therapy.

17 Claims, No Drawings

OTHER PUBLICATIONS

Loncin, J. F., et al., *Inorg. Chem.*, 25, 2646 (1986).
Moi, C. F., et al., *J. Am. Chem. Soc.*, 110, 6266 (1988).
Tweedle, M. F., et al., *J. Nuc. Med.*, 28, 705 (1988).
Goodwin, C. H., et al., *J. Nuc. Med.*, 27, 959 (1986).
Paik, C. H., et al., *J. Nuc. Med.*, 28, 572 (1987).
Paik, C. H., et al., *J. Nuc. Med.*, 29, 889 (1988).
Haseman, C. F., et al., *Eur. J. Nuc. Med.*, 12, 455 (1986).
Parker et al., *Pure & Appl. Chem.*, vol. 61, No. 9, 1637–1641 (1989).
Craig et al., *J. Chem. Soc. Chem. Commun.* (1989), pp. 794–796.
Cox et al., *J. Chem. Soc. Chem. Commun.* (1989), pp. 797–798.
Paik et al., *J. Nucl. Sci.*, vol. 30, No. 10, pp. 1693–1701 (Oct. 1989).
Paik et al., *Nucl. Med. Biol.*, vol. 16, No. 5, pp. 475–481 (1989).
Deshpande et al., *Nucl. Med. Biol.*, vol. 16, No. 6, pp. 587–597 (1989).
Deshpande et al., *The Journal of Nuclear Medicine*, "Copper-67-Labeled Monoclonal Antibody Lym-1, A Potential Radiopharmaceutical for Cancer Therapy: Labeling and Biodistribution in RAJI Tumored Mice", vol. 29, No. 2, pp. 217–225 (Feb. 1988).
Meares, Claude F., Protein Tailoring for Food and Medicine Uses edited by R. E. Feeny et al., *Attaching Metal Ions to Antibodies*, pp. 339–352 (1986).
Goodwin, D. A., et al., Abstract of "In Complex of a New Macrocyclic Bifunctional Chelator TETA", presented at European Nuclear Medicine Congress Meeting at Barbican, London, Sep. 3–6 (1985).
Meares et al., *Int. J. Cancer Suppl.*, 2, 99–102 (1988).
Meares et al., *Br. J. Cancer*, 62, 21–26 (1990).
Gransow et al., *ACS Symposium Series*, No. 241, "Generator Produced Bi-212" (1984).
Moi et al., *Anal. Biochem.*, 148, 249–253 (1985).

TETRA-AZA MACROCYCLES AND PROCESSES FOR THEIR PREPARATION

This is a continuation of Ser. No. 07/826,669, filed Jan. 29, 1992 now abandoned, which is a continuation of application Ser. No. 07/601,705, filed Oct. 30, 1990, now abandoned.

FIELD OF THE INVENTION

This invention relates to functionalised tetra-aza macrocycles, to metal complexes thereof, to conjugate compounds containing the functionalised tetra-aza macrocyles and metal complexes thereof and to their use in diagnosis and therapy.

BACKGROUND TO THE INVENTION

The attachment of metal ions to proteins, peptides and other, smaller molecules is a fast expanding technology, which has numerous proven and potential applications in research, in industry and, particularly, in medicine.

In recent years, much of the impetus behind the development of this technology has been the ability to link metal ions to antibodies, especially monoclonal antibodies. Such metal labelled antibodies have found a widespread use, especially in medicine, where they have been employed, for example, to target the metal ions to a specific tissue type, both in vitro and in vivo. Thus, metal labelled antibodies have applications in locating specific tissue types (e.g. employing computer-aided tomographic techniques where the metal ion is in some way detectable) and in the treatment of cell disorders (e.g. treating mammalian tumours where the metal ion is a cytotoxic radionuclide).

Conventionally, attachment of the metal ion to a protein such as an antibody has been achieved by complexation by an acyclic chelate such as a substituted diethylenetriaminepentaacetic acid [Gansow O. A. et al, Inorg. Chem., (1986), 25, 2772] or ethylenediaminetetraacetic acid [Meares, C. F. et al, Acc. Chem. Res., (1984), 17, 202] covalently linked to the antibody. Such acyclic complexes however tend to be unstable in vivo either as a result of acid-catalysed decomplexation or competitive chelate binding by $Ca^{2+}$ or $Zn^{2+}$ in serum, or as a result of competition from transferrin [Moerlein, S. M. et al, Int. J. Nuc. Med. Biol., (1981) 8, 277]. The lack of stability can result in uncomplexed metal atoms in the body which have a cytotoxic effect on healthy tissue (e.g. bone marrow) or which markedly reduce the signal-to-noise ratio of an imaging technique.

A possible alternative to the use of acyclic chelates in the labelling of antibodies is the use of macrocyclic ligands, which has previously been suggested in broad terms [Gansow ). A. et al, Am. Chem. Soc. Symp. Ser., (1984), 241, 215; UK patent Specification Publication No. 2122641; and Moi M. K. et al, Anal. Biochem., (1985), 148, 249-253]. More recently, tetra-azamacrocycles have been described which are capable of binding metals, and which can be conjugated to antibodies (International Patent Application Nos. WO 87/05030 and WO89/01476; and Moi M. K. et al J. Am. Chem. Soc., (1988), 110, 6266).

We have now found a new class of functionalised tetra-aza macrocycles, members of which are able to form kinetically inert complexes with metal ions. The macrocycles of the invention are particularly useful for attachment to proteins, especially antibodies, to provide conjugate compounds capable of binding metals, with good association rates, to give complexes which are advantageously stable in vivo and which posses an advantageous biodistribution profile.

SUMMARY OF THE INVENTION

Thus according to one aspect of the present invention we provide a compound of general formula (1):

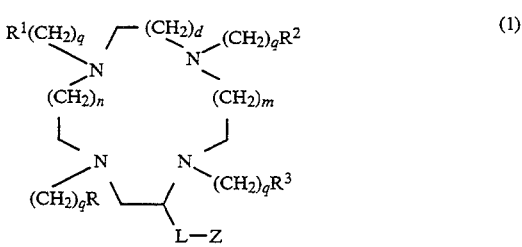

wherein
- m and n, which may be the same or different, is each zero or an integer 1, 2, or 3;
- d is zero or an integer 1, 2 or 3;
- q is zero or an integer from 1 to 6 inclusive;
- R, $R^1$, $R^2$ and $R^3$, which may be the same or different, is each a hydrogen atom or a group —P(O)(XH)$R^4$ (where X is an oxygen or sulphur atom and $R^4$ is a hydrogen atom or an alkyl or alkoxy group), with the proviso that at least one of R, $R^1$, $R^2$ and $R^3$ is a —P(O)(XH)$R^4$ group;
- is a covalent bond or a linker group;
- Z is a hydrogen atom or a reactive functional group;
- and metal complexes and/or salts thereof.

In the compounds of formula (1), alkyl groups represented by $R^4$ may be for example $C_{1-6}$alkyl groups such as methyl or ethyl groups.

Alkoxy groups represented by $R^4$ may be $C_{1-6}$alkoxy groups such as methoxy or ethoxy groups.

In general, compounds of formula (1) in which R, $R^1$, $R^2$ and $R^3$ are the same and is each a group —P(O)(XH)$R^4$ are preferred. Compounds of this type in which q is an integer from 1 to 6 inclusive, particularly an integer 1, are especially preferred. Particularly useful compounds of formula (1) are those wherein R, $R^1$, $R^2$ and $R^3$ is each a group —P(O)(OH)H, —P(O)(OH)CH$_3$, —P(O)(OH)OCH$_3$ or —P(O)(OH)OCH$_2$CH$_3$. In compounds of this type, q is preferably an integer from 1 to 6 inclusive, particularly an integer 1.

In the compounds of formula (1), it will be appreciated that the nature of the group L when it is a linker group may be varied widely without substantially affecting the usefulness of compounds of formula (1) and the metal complexes thereof. Thus L may be any suitable organic radical and may be for example an optionally substituted aliphatic hydrocarbyl chain, optionally interrupted by one or more heteroatoms selected from —O— or —S— or by one or more —N($R^5$)— (where $R^5$ is a hydrogen atom or a $C_{1-6}$alkyl group), —CON($R^5$)—, —N($R^5$)CO—, cycloaliphatic, aromatic, or heteroaromatic groups.

In the above definition, and in the same context whenever it appears below, the term "interrupted by" as applied to cycloaliphatic or aromatic groups is to be understood to also mean that these particular groups may additionally be present linked to the terminal carbon atom of the hydrocarbyl chain represented by L, at the opposite end of the chain to the carbon atom attached to the macrocycle.

Thus, for example, L may be an optionally substituted straight or branched $C_{1-20}$alkylene, $C_{2-20}$alkenylene, or $C_{2-20}$alkynylene chain, optionally interrupted by one or more —O— or —S— atoms or $C_{5-8}$cycloalkylene (e.g. cylcopentylene or cyclohexylene), $C_{6-12}$aromatic (e.g. phenylene or substituted phenylene), $C_{5-10}$heteroaromatic (e.g. furanyl, pyridyl), —N(R$^5$)—, —CON(R$^5$)— or —N(R)$^5$CO— groups.

Examples of substituents which may be present on the chain L include halogen atoms, e.g. fluorine, chlorine, bromine, or iodine atoms or groups selected from $C_{1-6}$alkoxy (e.g. methoxy or ethoxy), hydroxy, nitro, —N(R$^6$)(R$^7$), [where R$^6$ is a hydrogen atom or a $C_{1-6}$alkyl group and R$^7$ is a $C_{1-6}$alkyl group; e.g. —NHCH$_3$ or —N(CH$_3$)$_2$], or substituted amido, e.g. a group of formula —(CH$_2$)$_n$CON(R$^8$)(R$^9$) [where n is zero or an integer 1 to 4 inclusive, R$^8$ is a hydrogen atom or a $C_{1-6}$alkyl group, e.g. methyl and R$^9$ is an optionally substituted $C_{1-6}$alkyl group].

Substituted alkyl groups represented by R$^9$ include for example $C_{1-6}$alkyl groups substituted by one or more halogen atoms, or nitro, amino or hydroxy groups.

In general, in compounds of formula (1) the linker group is preferably an optionally substituted $C_{1-10}$alkylene, (especially $C_{1-6}$alkylene such as methylene, ethylene, propylene butylene, pentylene or hexylene) $C_{2-10}$alkenylene or $C_{2-10}$alkynylene chain optionally interrupted by one or more —O— or —S— atoms or cyclohexylene, phenylene, substituted phenylene, —NH—, —N(CH$_3$)—, —CONH—, —CONH(CH$_3$)— —NH-CO— or —N(CH$_3$)CO— groups.

Particular examples of linker groups represented by L include, for example, —(CH$_2$)$_d$— (where d is an integer 1 to 4 inclusive),

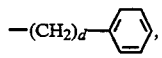

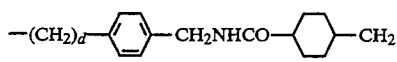

—(CH$_2$)$_d$NHCO(CH$_2$)$_e$— (where e is an integer 1 to 4 inclusive) and —(CH$_2$)$_d$NHCO(CH$_2$)$_e$OCH$_2$—.

The reactive functional group represented by Z in compounds of formula (1) may be any group capable of reacting with a thiol, amino, carboxyl, aldehyde, aromatic or heteroaromatic group. Aromatic groups include, for example, phenolic groups. Heteroaromatic groups include for example imidazolyl groups.

Thus, Z may be, for example, a halogen atom, for example a chlorine, bromine or iodine atom or a group selected from —SH, —NH$_2$, hydrazine (—NHNH$_2$) or a derivative thereof, [for example —N(CH$_3$)NH$_2$, —NHCONHNH$_2$, —NHCSNHNH$_2$, or phenyl hydrazine], —NCO, —NCS, —COR$^{10}$, [where R$^{10}$ is a halogen atom such as a chlorine or bromine atom, or a N$_3$, $C_{1-6}$alkoxy, e.g. methoxy, $C_{6-12}$aryloxy (e.g. nitrophenyloxy or dinitrophenyloxy), imidyloxy (e.g. succinimidyloxy) or imidazolyoxy group], imide, e.g. maleimide, a vinyl group of formula —Het$^1$—C(-Het$^2$)=CH$_2$ (where Het$^1$ and Het$^2$, which may be the same or different, is each a nitrogen containing heterocyclic group, e.g. a pyridyl group or Het$^1$ is a nitrogen containing heterocyclic group of formula

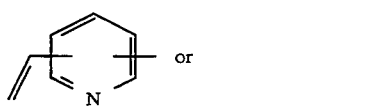

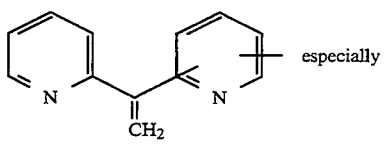

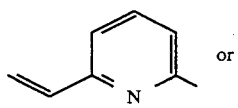

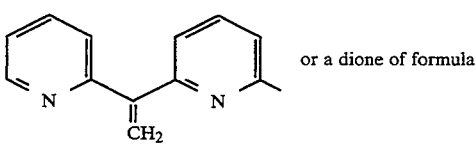

or a dione of formula

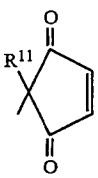

(where R$^{11}$ is a $C_{1-4}$ alkyl e.g. methyl, group).

Metal complexes of the compounds of formula (1) include complexes wherein the metal is di- or tripositive and has a coordination number 6 or greater, especially 8. Examples of such metals include indium (In), copper(Cu), lead (Pb), bismuth (Bi), yttrium (Y), gallium (Ga), terbium (Tb), gadolinium (Gd) and scandium (Sc). Y, Ga, Tb, Gd, Sc, and In are preferred, particularly In, Y, Gd and Ga. In general the metal is preferably a radioactive isotope. Yttrium, especially $^{90}$Y, is particularly preferred.

In general, optimum binding of the metal to the compounds of formula (1) may be achieved by selection of the ring size and where appropriate by adjusting the potential coordination number by choice of the group (CH$_2$)$_q$R, —(CH$_2$)$_q$R$^1$, —(CH$_2$)$_q$R$^2$, and/or —(CH$_2$)$_q$R$^3$. Thus a particularly important class of compound of formula (1) is that wherein d is an integer 1. Especially useful compounds are those wherein d is an integer 1, m is an integer 1 or 2 and n is an integer 1 or 2. In general, compounds of formula (1) in which —(CH$_2$)$_q$R, —(CH$_2$)$_q$R$^1$, —(CH$_2$)R$^2$ and —(CH$_2$)$_q$R$^3$ is each —CH$_2$P(O)(OH)R$^4$—where R$^4$ is —H, CH$_3$, —OCH$_3$ or —OCH$_2$CH$_3$ are particularly useful.

Salts of the compounds of formula (1) include salts with bases, e.g. sodium or potassium salts, or acid addition salts such as hydrobromides or hydrochlorides. Pharmaceutically acceptable salts are particularly preferred.

An important group of compounds according to the invention has the formulae (1a):

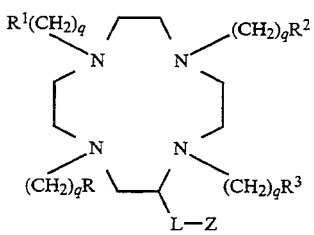

(1a)

wherein R, $R^1$, $R^2$, $R^3$, L and Z are as defined for formula (1) and metal complexes and/or salts thereof.

Compounds of this type in which R, $R^1$, $R^2$, and $R^3$ is each $P(O)(OH)R^4$ where $R^4$ is $-OCH_2CH_3$ or, especially, $-H$ or $-CH_3$ are particularly preferred.

q in compounds of formula (1a) is preferably an integer 1.

Compounds of formula (1a) in which L is a linker group [particularly those specifically identified for compounds of formula (1)] are especially useful.

Z in compounds of formula (1a) is preferably a reactive functional group, [particularly those specifically identified for compounds of formula (1)], especially a group of formula $-NH_2$, $-COR^{10}$, $-Het^1$ $-C(-Het^2)=CH_2$, an imide or a dione of formula

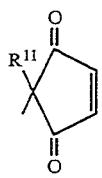

Indium, yttrium and gadolinium complexes of the compounds of formula (1a) are particularly useful.

A further group of compounds of formula (1a) which is particularly useful is that where in the compounds L is a covalent bond and Z is a hydrogen atom. Gadolinium complexes of compounds of this type are preferred, particularly gadolinium complexes of compounds of formula (1a) wherein q is an integer 1; R, $R^1$, $R^2$ and $R^3$ is each a group $-P(O)(OH)R^4$ where $R^4$ is $-H$ or $-CH_3$, L is a covalent bond; and Z is a hydrogen atom.

The compounds of formula (1) and the metal complexes and/or salts thereof have a diagnostic use as imaging agents in vitro and in vivo. The compounds of formula (1) and the metal complexes and/or salts thereof are also cytotoxic agents and may be of d in the treatment of abnormal cell disorders, for example in the treatment of tumours. For use as diagnostic and/or therapeutic agents, the compounds, may be employed using conventional methods, (e.g. for formulation and presentation) already in use for metal complexing reagents.

For application of the compounds of formula (1) as imaging or cytotoxic agents, it is generally preferable to couple the compounds to other molecules such as proteins, especially antibodies, peptides or carbohydrates to form conjugate compounds, and the compounds of formula (1) are particularly well adapted for use in this respect.

Thus, the compound of formula (1) may be coupled through any thiol, amino, carboxyl, hydroxyl, aldehyde, aromatic or heteroaromatic group present in the protein, peptide or carbohydrate.

In a preferred aspect of the invention, we provide a conjugate compound which comprises a compound of formula (1) or a metal complex and/or salt thereof, coupled to an antibody.

It is to be understood that a conjugate compound according to the invention may comprise more than one molecule of a compound of formula (1) coupled to any one protein, peptide or carbohydrate molecule.

In a particular aspect, the invention provides a conjugate compound of formula (2)

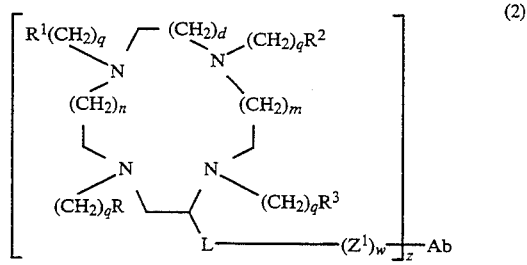

(2)

wherein m, n, d, q, R, $R^1$, $R^2$, $R^3$, and L are as defined for formula (1);

$Z^1$ is the residue of a reactive functional group;

w is zero or an integer 1;

z is an integer 1 or more;

Ab is an antibody; and metal complexes and/or salts thereof.

In the compounds of formula (2), the residue or a reactive functional group represented by $Z^1$ may in general be the residue of a reactive functional group Z as defined for formula (1).

In particular, $Z^1$ may be for example $-S-$, $-NH-$, $-NHN=$, $-N(CH_3)N=$, $-NHCONHN=$, $-NHCSNHN=$, $-N(Ph)N=$ (where Ph is phenyl), $-NC(O)-$,

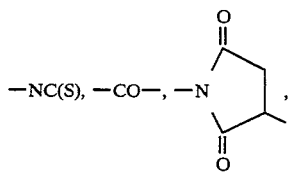

$-NC(S)$, $-CO-$, $-N$ $-Het^1-C(Het^2)CH_2-$ or

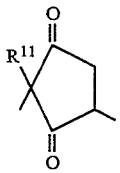

The antibody in the conjugates of formula (2) may in general belong to any immunoglobulin class. Thus for example it may be an immunoglobulin M antibody or, in particular, an immunoglobulin G antibody. The antibody molecule may be of animal, for example mammalian origin, and may be for example of murine, rat or human origin. It may be a natural antibody or a fragment thereof, or, if desired, a recombinant antibody or antibody fragment i.e. an antibody molecule or antibody fragment which has been produced using recombinant DNA techniques.

Particular recombinant antibodies or antibody fragments include, (1) those having an antigen binding site at least part of which is derived from a different antibody, for example those in which the hypervariable or complementarity determining regions of one antibody have been grafted into the variable framework regions of a second, different antibody (as described in European Patent Specification No. 239400); (2) recombinant antibodies or fragments wherein non-Fv sequences have been substituted by non-Fv sequences from other, different antibodies (as described in European Patent Specification Nos. 171496, 173494 and 194276; or (3) recombinant antibodies or fragments possessing substantially the structure of a natural immunoglobulin but wherein the hinge region has a different number of cysteine residues from that found in the natural immunoglobulin, or wherein one or more cysteine residues in a surface pocket of the recombinant antibody or fragment is in the place of another amino acid residue present in the natural immunoglobulin (as described in International Patent Applications Nos. WO89/01974 and WO89/01782 respectively).

The antibody may be of polyclonal or, preferably, monoclonal origin. It may be specific for any number of antigenic determinants, but is preferably specific for one. The antigenic determinants may be any hapten or antigenic determinant associated with any antigen. Particular antigens include those associated with animals, e.g. humans [for example normal animal tissue or organ cell-associated antigens, tumour cell-associated antigens (for example oncofetal antigens such as carcinoembryonic antigen or alphafetoprotein, placental antigens such as chorionic gonadotropin and placental alkaline phosphatase, and prostate antigens such as prostatic acid phosphatase and prostate specific antigen) and antigens associated with components of body fluids such as fibrin or platelets], viruses, bacteria and fungi.

In a preferred aspect the antibody may be capable of recognising and binding a tumour cell-associated antigen, particularly one or more epitopes on the TAG-72 antigen associated with human breast and colon tumours. A particularly preferred antibody of this type is the monoclonal antibody B72.3 [Colcher, D. et al Proc. Nat. Acad. Sci. USA (1981), 78 3199] or a fragment thereof, particularly a F(ab')$_2$ fragment.

The antibody Ab will in general be coupled to the remainder of the conjugate of formula (2) (i.e. the macrocycle and linker) through any appropriate reactive atom or group, for example a nitrogen or, especially, sulphur atom, present in the antibody. It will be appreciated that any one antibody molecule may contain more than one reactive group capable of coupling with the macrocycle and linker. Thus, for example, z in the conjugates of formula (2) may be an integer 1, 2, 3, 4, 5, 6 or more depending on the number of macrocycles linked to any particular antibody molecule or fragment.

Indium, and, especially, yttrium complexes of conjugates of formula (2) are particularly useful.

It is to be understood that the definition and preferences expressed for m, n, d, q, R, $R^1$, $R^2$, $R^3$ and L in compounds of formula (1), and for classes of compounds of formula (1) are also applicable to conjugates of formula (2).

Particularly useful conjugate compounds according to the invention are those comprising a compound of formula (1a), or a metal complex and/or salt thereof, coupled to an antibody. The indium and, especially, yttrium complexes of these conjugates are especially important.

The compounds of formulae (1) and (2) may be formulated for use in accordance with conventional practice, and thus according to a further respect of the invention we provide a composition comprising a compound of formula (1) or a compound of formula (2) or a metal complex and/or salt thereof, together with one or more pharmaceutically acceptable carriers.

Particularly suitable compositions according to the invention are those adapted for parenteral administration, especially intravenous administration. Suitable formulations of this sype include solutions of the compounds of formulae (1) or (2) in isotonic saline.

The quantities of compounds of formulae (1) or (2) used in formulations according to the invention will vary according to the intended use (i.e. imaging or therapy) and other variables such as the intended cell target, but may be easily determined in accordance with conventional practice for reagents of this type.

Compounds of the invention may be prepared by the following processes wherein the groups and symbols R, $R^1$, $R^2$, $R^3$, m, n, d, q, L, Z, Ab and z are as defined for formulae (1) and (2) except where stated otherwise. Where a metal complex is desired as a final product, the complexation with a metal atom may be carried out as a final step in the production process, as described below for the complexation of compounds of formulae (1), or alternatively it may be desirable to complex the metal at an earlier stage in the process, providing of course that the requisite macrocycle structure is present. In the following processes, it may be desirable to use starting materials in which the group Z is in a protected state, or which contain a precursor of the group, as discussed below.

Thus, according to a further aspect of the invention a compound of formula (1) [wherein q is an integer 1-6 and, where present, the group X is an oxygen atom] or a metal complex thereof may be prepared by reaction of a corresponding compound of formula (3)

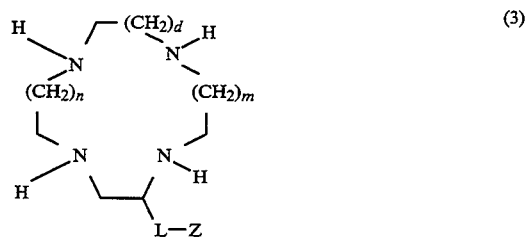

(3)

or a metal complex thereof, with a reagent
$D(CH_2)_qP(O)(OR^{13})R^4$ or $D(CH_2)_qP(O)(OR^{13})_2$ (where D is a displaceable group, for example a halogen atom such as a bromine atom or a sulphonyloxy group, such as a methanesulphonyloxy group; $R^{13}$ is a $C_{1-4}$ alkyl, e.g. methyl or ethyl group; and q and $R^4$ are as defined previously) followed where necessary by hydrolysis.

The reaction may be performed in a solvent such as water or an organic solvent such as a nitrile e.g. acetonitrile or an alcohol, e.g. ethanol or an amide e.g. dimethylformamide in the presence of a base such as an alkali metal carbonate or hydroxide, e.g. sodium, potassium or caesium carbonate, or sodium, potassium or lithium hydroxide, at an elevated temperature e.g. the reflux temperature.

Where appropriate, hydrolysis may be achieved using a base, such as described above, in a suitable solvent, for example sodium hydroxide in an alcohol such as ethanol.

In this reaction, the group Z may need to be in a protected state. Conventional protecting groups may be used, depending on the nature of Z, and may be removed using standard procedures, once the desired reaction has been effected.

Reagents $D(CH_2)_qP(O)(OR^{13})R^4$ and $D(CH_2)_qP(O)(OR^{13})_2$ may be prepared by heating compounds of formulae $P(OR^{13})_2R^4$ or $P(OR^{13})_3$ with a compound $CH_2D_2$.

In another process, a compound of formula (1) may be prepared by reaction of a compound of formula (3) or a metal complex thereof with a phosphine $R^4P(OR^{13})_2$ and an aldehyde (for example formaldehyde or paraformaldehyde), followed by hydrolysis.

The reaction may be performed in an organic solvent e.g. a nitrile, alcohol or amide, or an ether such as tetrahydrofuran, at an elevated temperature, for example the reflux temperature. Hydrolysis may be achieved using an acid, for example an inorganic acid such as hydrochloric acid, at an elevated temperature such as the reflux temperature.

Compounds of formula (1) may also be prepared by interconversion from other compounds of formula (1). Thus one functional group Z may be exchanged for another and, if desired a linker group L changed to another by appropriate manipulative reactions. For example, a compound of formula (1) where —L—Z is a group —L¹—NHCO—L²—Z (where —L¹—NH-CO—L² represents the group L) may be prepared by reaction of a corresponding compound wherein —L—Z represents —L¹—NH₂ with a reagent $R^bO$—L²—Z (where $R^b$ is for example am imide, such as succinimide, or a substituted phenyl group such as a p-nitrophenyl group) in the presence of a tertiary amine, such as diisopropylethylamine, is a solvent such as dimethylformamide.

Reagents of formula $R^bO$—L²—Z are either known compounds or may be obtained from known starting materials using methods analogous to those used for the preparation of the known compounds.

In another interconversion process, a compound of formula (1) wherein X where present is a sulphur atom may be prepared by reaction of a corresponding compound wherein X is an oxygen atom by reaction with a sulphide, for example phosphorous pentasulphide, at an elevated temperature.

It will be appreciated that where it is desired to prepare a compound of formula (1) in which R, R¹, R² and R³ are not the same this may be achieved by first selectively N-protecting the compound of formula (3) or a precursor using an appropriate amine protecting group(s), for example a p-toluenesulphonyl group as described below, in accordance with conventional practice. Reaction of the N-protected compound (3) using the methods described above followed by deprotection and further reaction as necessary then yields the desired compound in which R, R¹, R² and R³ are not the same.

Where metal complexes of compounds of formulae (1) or (2) are required (or any other suitable macrocyclic intermediate described herein) these may be prepared by treating the compound with a metal salt (for example a metal halide) in an appropriate solvent for example an aqueous or non aqueous solvent, (e.g. acetonitrile, acetone, propylene carbonate, dimethylformamide or dimethylsulphoxide) at any suitable temperature from 0° C. to 100° C. such as 10° e.g. around 60° C.

A conjugate compound of formula (2) or a metal complex thereof may be prepared by reaction of a corresponding compound of formula (1) or a metal complex thereof with an antibody Ab (as previously defined).

The reaction may be performed in a suitable solvent, for example an aqueous solvent such as a phosphate buffer, at an appropriate temperature, for example at 0°C.-30° C., especially 0°-10° C. e.g. 4° C.

The antibody Ab may be obtained using procedures well known in the art. If desired, before the coupling reaction, the antibody may first be treated to yield appropriate groups for reaction with the compound of formula (1). Thus for example the antibody may be subjected to oxidation, for example periodate oxidation to yield aldehyde groups, or, in particular, may be treated with a reagent [e.g. Traut's reagent (2- iminothiolane)] using standard procedures to generate free sulphydryl groups in the molecule.

Salts of compounds of formulae (1) or (2) and their metal complexes may be prepared by conventional means, for example by reaction with an appropriate base or acid in a suitable aqueous solvent.

Intermediate of formula (3) may be prepared by deprotection of a compound of formula (4)

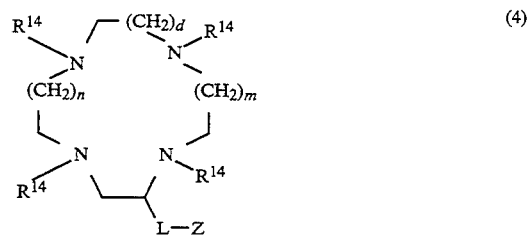

(where $R^{14}$ is a protecting group such as a p-toluenesulphonyl group). The deprotection will depend on the nature of the protecting group $R^{14}$. Thus, for example, when $R^{14}$ is a p-toluenesulphonyl group removal of this may be achieved by treatment of the compound of formula (4) with an acid, for example HBr-acetic acid, in the presence of phenol at a high temperature, or by reaction with lithium and liquid ammonia in a solvent such as tetrahydrofuran in the presence of an alcohol such as ethanol.

Intermediates of formula (4) may be prepared by treating a compound of formula (5)

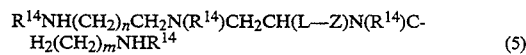

with a compound $R^{14}OCH_2(CH_2)_dOR^{14}$ in the presence of a base such as sodium ethoxide or caesium carbonate in a solvent such as dimethylformamide.

Intermediates of formula (5) may be prepared by reaction of compounds of formula (6)

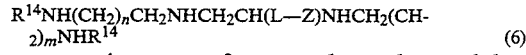

with a protecting agent, for example p-toluenesulphonyl chloride in a base such as pyridine.

Intermediates of formula (6) in which m and n are the same may be prepared by reaction of a diamine of formula (7):

with a reagent $R^{13}NH(CH_2)_mCOHal$ (where Hal is a halogen atom) in the presence of a base such as triethylamine, followed by reduction using for example borane in a solvent such as tetrahydrofuran at a high temperature e.g. the reflux temperature, followed by treatment with an acid such as hydrochloric acid.

Where it is desired to prepare an intermediate of formula (9) in which m and n are not the same a protected amine H$_2$NCH(L—Z)CH$_2$NHR$^{14}$ may be used in the above reaction. Removal of the protecting group after the reaction followed by repeated alkylation with a different compound R$^{14}$NH(CH$_2$)$_n$COHAl then yields the required intermediates.

Diamines of formula (7) may be prepared from an appropriately substituted amino acid of formula (8):

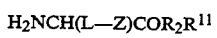  (8)

by reaction with ammonia in a solvent such as methanol, followed by reduction using for example lithium aluminim hydride.

The substituted amino acids of formula (8) are either known compounds or may be prepared using methods analogous to those used for the preparation of the known compounds.

In an alternative process, intermediates of formula (5) may be prepared by reaction of a compound of formula (9)

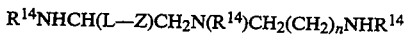  (9)

with a compound R$^{14}$OCH$_2$(CH$_2$)$_d$N(R$^{14}$)(CH$_2$)$_m$C-H$_2$OR$^{14}$ in the presence of a base such as caesium carbonate in a solvent such as dimethylformamide.

Intermediates of formula (9) may be prepared by reduction of compounds of formula (10):

  (10)

using for example borane as described above, followed by reaction to introduce the protecting group R$^{14}$, for example with p-toluenesulphonyl chloride in a solvent such as dichloromethane in the presence of a base such as triethylamine at e.g. reflux.

Intermediates of formula (10) may be prepared by reaction of an appropriately substituted amino acid of formula (8) (where R$^{11}$ is a methyl or ethyl group) with a diamine H$_2$NCH$_2$(CH$_2$)$_n$NH$_2$ at a high temperature, e.g. the reflux temperature.

DESCRIPTION OF SPECIFIC EMBODIMENTS

The invention is illustrated by the following Intermediates and Examples.

INTERMEDIATE 1

2,6-Diamino-1-hexanoic acid, ethylenediamine ester 2,6-Diamino-1-hexanoic acid, methyl ester, dihydrochloride (10.283 g) was added (as solid) in small batches over a 50 minute period to ethylenediamine (100 ml) at 90° C., with stirring. The temperature of the reaction mixture was then raised to 140° C. for 6 hrs, after which the ethylenediamine was removed by vacuum distillation to yield a brown residual oil which was taken up in 4M NaOH (25 ml) and dried in vacuo. Methanol (30 ml) was added, the solution was filtered, the methanol removed (Buchi) and the residue dissolved in CH$_2$Cl$_2$ (100 ml), then filtered, and the filtrate rotovated down to give the title compound as a clear brown oil (8.827 g). i.r. (thin film) 3300/3280 3060 2930 2860 1650 1570 1470 1320 cm$^{-1}$.

INTERMEDIATE 2

1,5,9-Triamino-3-aza-nonane, tetrahydrochloride

Intermediate 1 (3.754 g) and borane-tetrahydrofuran (130 mmol, 130 ml) was refluxed for 21 hours. After removal of volatiles, the aminoborane was washed with methanol (2×100 ml) and hydrolysed with 6M HCl (150 ml, 110° C.) for 3 hours. The resulting solution was evaporated, methanol (20 ml) added and further evaporated to yield the title compound (6.279 g) as a white hygroscopic solid.

INTERMEDIATE 3

1,5-Diamino-(9-N-benzamidyl)-3-aza-nonane

Intermediate 2 (6.16 g) and potassium hydroxide (4.4 g) was dissolved in water (50 ml) and, with stirring, copper carbonate (2.603 g) was added. Continued stirring over 30 minutes at 50° C. yielded an intense blue solution which was cooled to 0° C. and benzoyl chloride 2.5 ml added in 0.25 ml portions over 90 minutes keeping the pH greater than 9 with periodic addition of KOH pellets. The solution was then allowed to stir at room temperature for 1 hour, then filtered and the filtrate treated with H$_2$S over 30 minutes. The solution was filtered once again to give a greeny-yellow filtrate which on addition of KOH to pH14 went a dark green, with a small amount of green precipitate. This was filtered off, the filtrate reduced in volume to 40 ml and exhaustively extracted (13×) with CH$_2$Cl$_2$, dried (K$_2$CO$_3$), and evaporated to yield the title compound as a pale yellow oil (2.152 g). $^1H$-NMR (250 MHz), (CDCl$_3$): 1.57 (m, 16H, CH$_2$, NH, NH$_2$) 2.37 (dd, 1H, CH), 2.67 (m 3H, CH$_2$N), 2.79 (m, 3H, CH$_2$N).

INTERMEDIATE 4

1,5-Ditosylamino-3-tosyl-(9-N-benzamidyl)-3-aza-nonane

Intermediate 3 (1.978 g) in dry CH$_2$Cl$_2$ (50 ml) was added dropwise to a solution of tosyl chloride (5.087 g), in dry CH$_2$Cl$_2$ (50 ml) and the mixture was then allowed to stir for 2 ½ hours at room temperature. The solution was then washed with water (20 ml) dried (K$_2$CO$_3$), filtered and evaporated to an oily brown residue which was redissolved in CH$_2$Cl$_2$ (10 ml). After a few minutes a white solid precipitated which was collected by filtration and washed with CH$_2$Cl$_2$ to give the title compound (1.701 g). TLC (silica; 5% methanol in CH$_2$Cl$_2$) Rf 0.44 m/e [desorption chemical ionisation (methanol)] 741 (M+ +1), 740 (M+).

INTERMEDIATE 5

2-(4-N-Benzamidyl)butyl-N,N',N'',N'''-tetratosyl-1,4,7,10 tetraazacyclododecane

Intermediate 4 (1.116 g) was dissolved in anhydrous dimethylformamide (100 ml) and caesium carbonate (1.032 g) added under dry nitrogen. A solution of TsO(CH$_2$)$_2$N(Ts)(CH$_2$)$_2$OTs(0.855 g; where Ts represents tosyl), in anhydrous dimethylformamide (40 ml) was slowly added, with stirring, over 3 hours. Stirring was continued at room temperature for 20 hours. The dimethylformamide was removed under reduced pressure and the residue dissolved in chloroform (200 ml), washed with water (3×30 ml) and dried (K$_2$CO$_3$) to yield the title compound. m/e [desorption chemical ionisation (iso-but)]: 964 (M+ +1), 963 (M+).

INTERMEDIATE 6

2-(4-N-Benzamidyl)butyl-1,4,7,10-tetraazacyclododecane

The title compound was prepared from Intermediate 5 by the method described in International Patent Specification No. WO 89/01476.

EXAMPLE 1

Preparation of a compound of formula (1a) wherein q is an integer 1, L is —(CH$_2$)$_4$—, Z is —NH$_2$ and R, R$^1$, R$^2$, and R$^3$ is each a group —P(O)(OCH$_2$CH$_3$)CH$_3$.

BrCH$_2$P(O)(OCH$_2$CH$_3$)CH$_3$ [m/e (ci) 201/203 (M$^+$ +1); p(CDCl$_3$) +47.1 (s); $_H$(CDCl$_3$) 4.10 (2H, dq, CH$_2$O); 3.43 (2H, d, J=7, CH$_2$Br), 1.60 (3H, d, P-CH$_3$, J=14), 1.23 (3H, t, J=7) prepared by heating CH$_2$Br$_2$ and CH$_3$P(OCH$_2$CH$_3$)$_2$] in dimethylformamide (5 ml) containing K$_2$CO$_3$, in a molar ratio of 2:1. The mixture was heated at 80° C. under nitrogen and further base and bromo-derivative added as necessary until HPLC analysis revealed that the reaction was essentially complete. The solvent was then removed in vacuo and, after filtration, the product was dissolved in 6M hydrochloric acid (10 ml) and heated to 140° C. under nitrogen overnight. The reaction mixture was then concentrated in vacuo and co-evaporated with dry dimethylformamide to yield the compound of formula (1a) described above, which was then hydrolysed to the corresponding tetraacid (i.e. where R, R$^1$, R$^2$ and R$^3$ is each —P(O)(OH)CH$_3$ using hydrochloric acid as described in Example 2.

EXAMPLE 2

Preparation of a compound of formula (1a) wherein q is an integer 1, L is —(CH$_2$)$_4$—, Z is —NH$_2$ and R, R$^1$, R$^2$ and R$^3$ is each a group —P(O)(OH)CH$_3$.

(a) To a solution of Intermediate 6 (0.36 g) in dry tetrahydrofuran (25 ml) was added diethoxymethylphosphine (0.65 g) and then paraformaldehyde (0.18 g) and the mixture was heated to reflux for 24 h with removal of water (Soxhlet, 4A molecular sieves). After filtration and evaporation of solvent, the residue was purified by chromatography on neutral alumina (0 - - - 3% MeOH in CH$_2$Cl$_2$) to yield a colourless oil (0.253 g) Rt (CM300, 'standard' conditions)=5.7 min. $\partial_H$ (CDCl$_3$) 1.18–1.23 (12H, mult, CH$_3$CH$_2$), 1.25–1.50 (18H, mult, CH$_3$P+CH$_2$C), 2.23–3.82 (25H, mult., CH$_2$N ring+CH$_2$P+CH$_2$NHCO), 3.93–4.03 (8H, mult., CH$_2$)), 7.34 (3H mult., aryl CH), 7.66 (1H, brt, NHCO) 8.07 (2H, dd, ortho CH).

$\partial$p (CDCl$_3$) 50.4–52.3 (mult). $\partial_C$ (CDCl$_3$) 164.8 (CONH), 132.5 (s, C$_6$H$_5$CO); 128.3, 125.5, 124.7 (CH arom); 60.5 (CH$_2$O); 59.2, 58.2, 58.1, 58.0, 56.8, 56.3, 55.9, 55.0, 54.7, 51.7, 51.5, 51.0, 49.7 (CH$_2$N diastereoisomers), 40.9 (CH$_2$NHCO), 31.0 (br.s., CH$_2$C); 29.6, 29.5 (CH$_2$C)-26.4 (CH$_2$C); 19.2 (CH$_3$CH$_2$); 16.1 and 15.9 (d+d, Jep 91 Hz, CH$_3$P diastereoisomers (3:1)). max (film) 3400, 3200 (NH); 2965, 2910, 2820 (CH); 1645 (s., NHCO), 1205 (vs) 1035 (vs), 954 (s) cm$^{-1}$. m/e (d.c.i.) 829 (M$^+$ +1).

(b) A solution of the tetraester (0.185 g) of Part (a) in hydrochloric acid (6M, 25 ml) was heated to reflux for 48 h. After cooling, washing with ether (2×5 ml), dichloromethane (2×5 ml) and evaporation under high vacuum (0.01 mm Hg) a colourless glass was obtained of the tetrahydrochloride salt of the compound of the Example (0.153 g). $\partial_H$(D$_2$O) 4.1–2.5(25H,m)1.9–1.1(118H,m).

EXAMPLE 3

To a solution of the tetraacid Example 2(63.2 mg) and N-methylmorpholine (72.5 mg) in dry dimethylsulphoxide (1.5 ml) was added a solution of N-succimimidyl-3-maleimidopropionate (42.4 mg,) in dry dimethylsulphoxide (1.0 ml). The mixture was stirred overnight at 20° C. and the reaction was monitored by HPLC (Dynamax C18 60A 21.4 mm column, A=0.1% TFA-H$_2$O, C=0.1% TFA-MeCN: t=0 A=95%, C=5%, t=20 mins. A=5% C=95%; flow=10.0 ml/min). Reaction was essentially complete after 3 h.

The reaction mixture was purified by HPLC (Dynamax CI8 60A 21.4 min column; A=0.1% TFA-H$_2$O, C=0.1% TFA-MeCN: t=0 A95% C=5%, t=20.0 mins A=55% C=45%, flow=10.0 ml/min) to yield as a colourless solid (50.0 mg) the compound of formula (1a) in which q is an integer 1, L is —(CH$_2$)$_4$-1, Z is

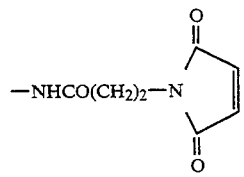

and R, R$^1$, R$^2$ and R$^3$ is each a group —P(O)(OH)CH$_3$. m/e (FAB, m-nitrobenzylalcohol) 763 (M$^+$ +1); S$_H$ (D$_2$O) 6.64 (2H, 5), 4.0–2.6 (27H, 6 m. N—CH$_2$, N—CH, OCN CH$_2$, CH$_2$P), 2.5 ppm (6H, S)-1 molecule DMSO complexed, 2.26 (2H, t, J=CH$_2$—C) and 1.8–1.0 ppm (18H, 6 m overlapped doublets at 1.2 ppm, —CH$_2$—, CH$_3$—P).

EXAMPLE 4

(a) To a solution of 1,4,7,10-tetraazacyclododecane (0.5 g) in dry tetrahydrofuran (30 ml) was added diethoxymethylphosphine (2.37 g) and paraformaldehyde (1.13 g) and the mixture was heated to reflux with azeotropic removal of water (Soxhlet, 3A sieves). After 18 h solvent was removed under reduced pressure and the residue was purified by chromatography on alumina (0 2% CH$_3$OH in CH$_2$Cl$_2$) to yield as a pale yellow oil the compound of formula (1a) in which q is an integer 1, L is a covalent bond, Z is —H and R, R$^1$, R$^2$ and R$^3$ is each a group —P(O)(OCH$_2$CH$_3$)CH$_3$ (948 mg). RF 0.5 (5% MeOH/CH$_2$Cl: Al$_2$O$_3$). $\partial$p (CDCl$_3$) 51.6, 51.8, 51.9 (diastereoisomers) $\partial_C$ (CDCl$_3$) 13.44 (d, J$_{CP}$91 Hz, PCH$_3$), 16.42 (CH$_3$), 54.18 (CH$_2$N ring), 54.30 (d, J$_{CP}$ 110 Hz, CH$_2$P), 59.82 (CH$_2$O). $\partial_H$ (CDCl$_3$) 1.31 (12H, t, CH$_3$CH$_2$), 1.57 (12H, d, J=13.7 Hz, CH$_3$P), 2.64–3.07 (24H, mult., CH$_2$N), 4.07 (8H, dq, CH$_2$O). m/e (d.c.i.) 652(M$^+$), 533 (M$^+$-PC$_3$H$_8$O$_2$).

(b) The tetraester (115 mg) in hydrochloric acid (6M, 20 ml) was heated to reflux (110° C.) for 36 h. After removal of solvent and drying under vacuum (40° C., 0.01 mmHg) a glassy foam was obtained. $\partial$(D$_2$O) 41.03. $\partial_c$(D$_2$O) 14.86 (d, J$_{CP}$94 Hz, CH$_3$P), 50.70 (CH$_2$N), 51.64 (d, J$_{CP}$, 118.3 Hz, CH$_2$P) $\partial_H$ (D$_2$O) 1.41 (12H, d, J=14.1 Hz, CH$_3$P), 3.37 (24H, br, CH$_2$N) m/e (negative FAB, glycerol) 540$^+$ (M$^+$), 539 (M$^+$-1), 538 (M$^+$-2).

(c) Preparation of the Yttrium Complex

To a solution of the tetraphosphinic acid of Part b (99 mg) in MilliQ water (10 ml) was added yttrium oxide (20.8 mg) and the suspension was heated at 80° C. for 2 h. After removal of solvent a colourless glass was obtained. m/e (negative FAB, glycerol) 625 ($M^-$), 626 ($M^-+1$). $\partial_C(D_2O, pD=0.7)$ 15.7 (d, $J_{CP}$96 Hz, $PCH_3$), 52.1 (d, $CH_2P$), 50.6 ($CH_2N$, br). $\partial_H(D_2O)$ 1.41 and 1.39 (12H, d+d, (ratio 3:1), $J_{PH}=14.5$ and 14.1 Hz), 3.20 (24H, brs, $CH_2N$).

(d) Preparation of the Gadolinium Complex

The gadolinium (111) complex of the acid of Part b was prepared as described above using 400 mg of the acid and 133 mg of $Gd_2O_3$. The suspension dissolved within 30 min. of mixing at 70° C. and the resultant glassy solid was stable (with respect to formation of insoluble $Gd(OH)_3$) at pH 11.

(e) Preparation of the $^{90}Y$ Complex

To a solution of the tetraphosphinic acid of Part b (5 $\mu \partial m^3$) in tetramethylammonium morpholinoethanesulphate (MES) buffer (0.1M, pH, 6.8, 90 $\mu \partial m^3$) at 37° C. was added 5 $\mu Ci$ of 90Y (5 $\mu \partial m^3$ of an aqueous solution of the trichloride). After 0.5 h, the mixture was analysed by HPLC (AX 300: 0.2M $NH_4OAc$: 10% $CH_3CN$) with radiometric detection (LKB radiation detector) following quenching of the labelling reaction by addition of a 500 fold excess of diethylenetriaminepentaacetic acid DTPA. Radiolabelling yields of 82% were determined (hplc radiometry integrating the $^{90}Y$-ligand peak (4.5 mins.) against $^{90}Y$-DTPA. (15 mins.). After maintaining the complex at this pH at 298K in the presence of a 500 fold excess of DTPA, no change in the relative concentration of complex was deserved at 24, and 72 h.

We claim:

1. A compound of the formula:

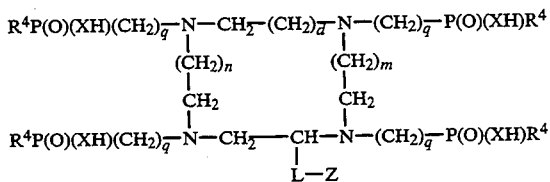

wherein
m has a value of from 0 to 3;
n has a value of from 0 to 3;
d has a value of from 0 to 3;
q has a value of from 0 to 6;
X is oxygen or sulphur;
$R^4$ is hydrogen, alkyl, or alkoxy;
L is a linker group; and
Z is a reactive functional group;
and metal complexes and/or salts thereof.

2. A compound according to claim 1 wherein q is 1 and X is oxygen.

3. A compound according to claim 1 wherein L is an aliphatic hydrocarbyl chain, which is optionally interrupted by —O—, —S—, —N($R^5$)—, —CON($R^5$)—, —N($R^5$)CO—,
in which $R^5$ is hydrogen or $C_{1-6}$alkyl, or a cycloaliphatic, aromatic, or heteroaromatic group.

4. A compound according to claim 1 wherein Z is a group capable of reacting with a thiol, amino, carboxyl, aldehyde, aromatic or heteroaromatic group.

5. A compound according to claim 1 wherein d is 1 and each of n and m is 1.

6. A compound according to claim 5 wherein X is oxygen.

7. An indium, yttrium, gallium or gadolinium complex of a compound according to claim 1.

8. An yttrium complex of a compound according to claim 1.

9. A gadolinium complex of a compound according to claim 1.

10. A conjugate compound of the formula:

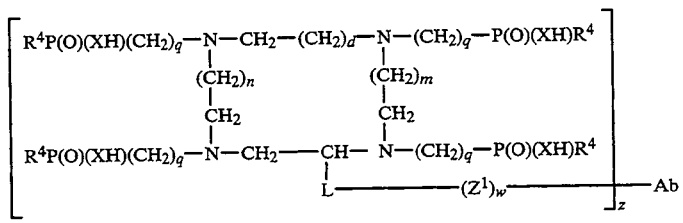

wherein
m has a value of from 0 to 3;
n has a value of from 0 to 3;
d has a value of from 0 to 3;
q has a value of from 0 to 6;
X is oxygen or sulphur;
$R^4$ is hydrogen, alkyl, or alkoxy;
L is a linker group; and
Z is a reactive functional group;
$Z^1$ is the residue of a reactive functional group;
w is 0 or 1;
z is an integer 1 or more; and
Ab is an antibody;
and metal complexes and/or salts thereof.

11. A conjugate compound according to claim 10 wherein q is 1 and X is oxygen.

12. A conjugate compound according to claim 10 wherein L is an aliphatic hydrocarbyl chain, which is optionally interrupted by —O—, —S—, —N($R^5$)—, —CON($R^5$)—, —N($R^5$)CO—, in which $R^5$ is hydrogen or $C_{1-6}$alkyl, or a cycloaliphatic, aromatic or heteroaromatic group.

13. A conjugate compound according to claim 10 wherein d is 1 and each of n and m is 1.

14. A conjugate compound according to claim 13 wherein X is oxygen.

15. An indium, yttrium, gallium or gadolinium complex of a conjugate compound according to claim 10.

16. An yttrium complex of a conjugate compound according to claim 10.

17. A gadolinium complex of a conjugate compound according to claim 10.

* * * * *